United States Patent [19]

Malenchek

[11] Patent Number: 5,425,721
[45] Date of Patent: Jun. 20, 1995

[54] NEEDLE PROTECTIVE DEVICE

[76] Inventor: Robert Malenchek, 279 Sunnymead Rd., Somerville, N.J. 08876

[21] Appl. No.: 308,382

[22] Filed: Sep. 19, 1994

[51] Int. Cl.⁶ ............................................. A61M 5/32
[52] U.S. Cl. ..................................... 604/198; 604/263
[58] Field of Search ............... 604/198, 187, 110, 263, 604/164, 171; 128/763, 764, 765

[56] References Cited

U.S. PATENT DOCUMENTS

| 5,295,974 | 3/1994 | O'Laughlin | 604/198 |
| 5,336,199 | 8/1994 | Castillo et al. | 604/198 |
| 5,360,408 | 11/1994 | Vaillancourt | 604/263 X |
| 5,368,568 | 11/1994 | Pitts et al. | 604/263 X |

Primary Examiner—John D. Yasko
Attorney, Agent, or Firm—Omri M. Behr; Matthew J. McDonald

[57] ABSTRACT

A thermoplastic housing formed of two mirror image halves snap fitted together has first and second resiliently cantilevered channeled ramps each having mating halves on opposite sides of a housing chamber. The ramps are on first and second angularly spaced axes aligned with a first needle receiving opening. A needle extends from a cylindrical body having an enlarged collar, the body being received between the first ramp halves with the needle protruding through the opening from the housing chamber and the collar restrained by the first ramp halves at corresponding coplanar collar edges. A spring surrounds the needle and abuts the body and housing urging the collar into axial locked engagement with the oppositely spaced first ramp halves. A cam displaces the body to the second axis wherein the spring forces the body rearwardly until the collar engages the edges of the halves of the resilient second ramp and a shoulder formed in the housing placing the needle wholly within the chamber and locking the needle assembly in opposite axial directions.

20 Claims, 4 Drawing Sheets

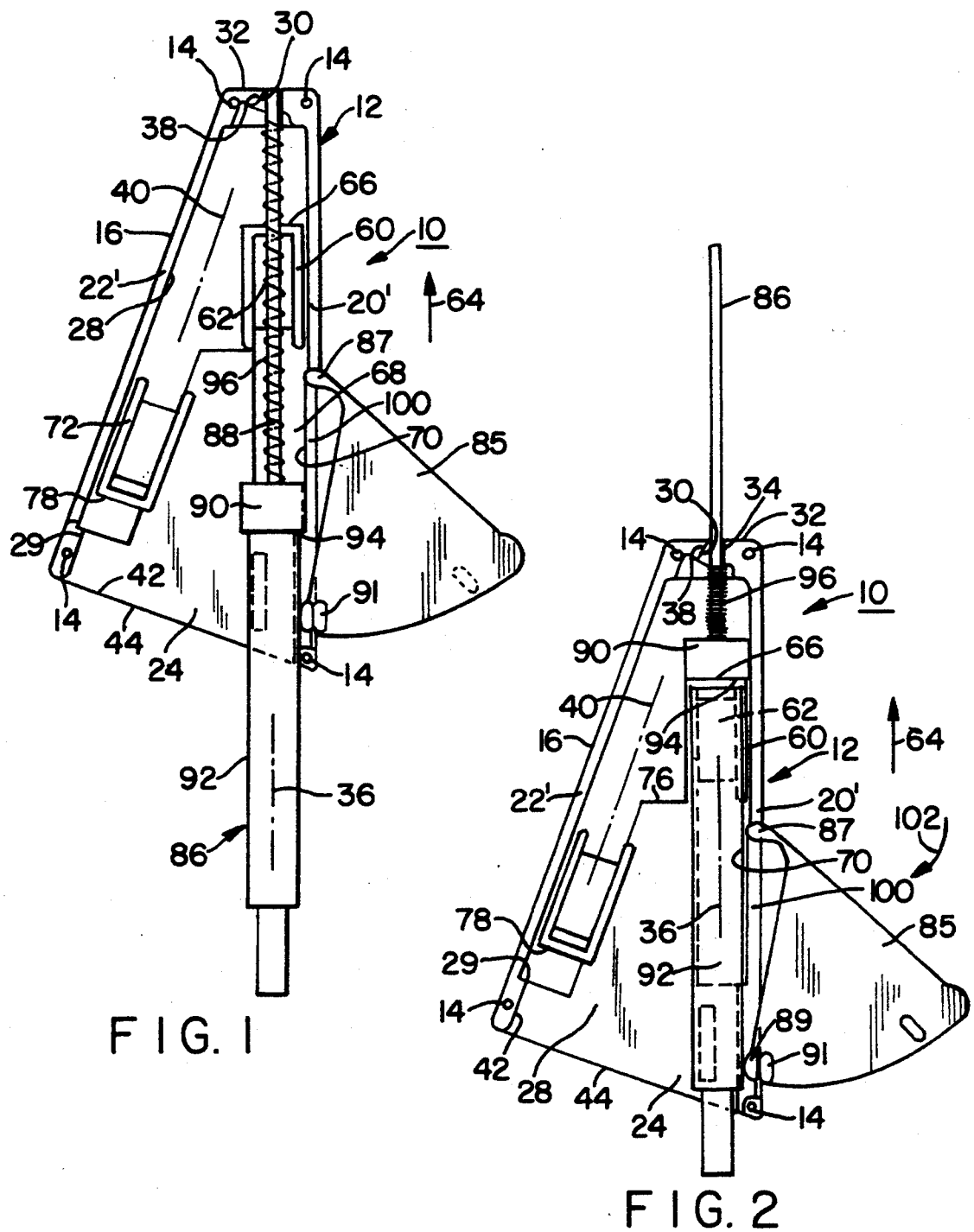
FIG. 1
FIG. 2
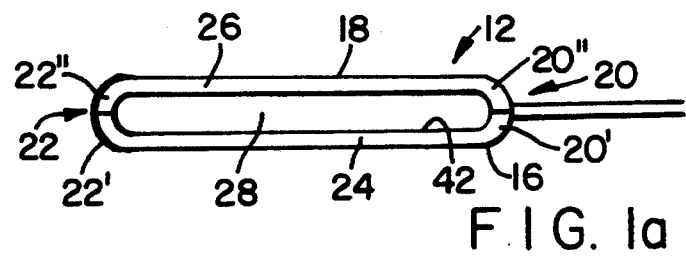
FIG. 1a

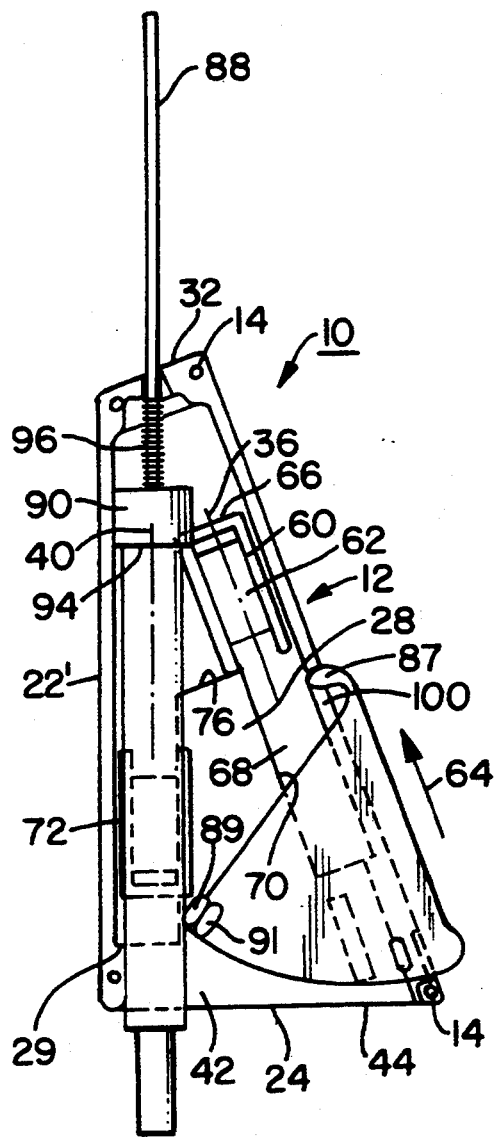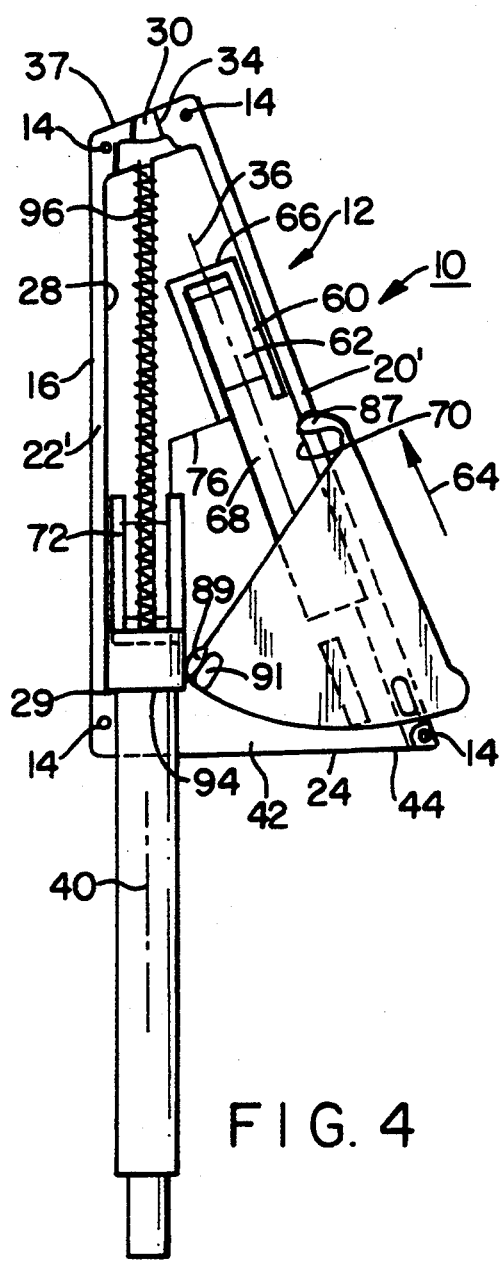
FIG. 3
FIG. 4

NEEDLE PROTECTIVE DEVICE

This invention relates to needle protective devices, more particularly, protective devices used to protect hypodermic and catheter needles and the like.

Needle protective devices are in wide use. They typically comprise inner and outer cylindrical members with mating locking ribs and grooves and similar locking devices. The locking ribs and grooves temporarily lock the outer protective member in a first mode wherein the needle is exposed and projects from the protective device. This locking position is to preclude the members from accidentally engaging their locking devices in a permanent needle protective locking position prior to use of the needle. Some devices include cylinders which may receive a syringe in a hyperdermic application, may be a vacuum cartridge having a septum which is penetrated by a needle portion inside the bore of a receiving cylinder in a blood collecting application or a catheter used for intravenous purposes.

In a blood collecting unit, a blood collecting needle portion projects beyond the cylinder. When its use is completed the outer cylinder member is axially displaced from an overlying position with the inner member to a position cantilevered from the inner member and locked into a needle protective position.

U.S. Pat. No. 4,894,055 discloses multiple tubular members. U.S. Pat. No. 5,098,382 employs a complex arrangement of multiple components. PCT application WO 89/09076 discloses a device which only partially protects the exposed needle. U.S. Pat. No. 4,966,592 employs a slidable sleeve for receiving a hypodermic syringe. An angularly engagable pin and slot define limits of extension and retraction for use with a syringe. Other devices employ complex lever mechanisms as disclosed in U.S. Pat. Nos. 5,026,356; 4,311,136; and 5,069,667.

The problem recognized by the present invention is that the prior art devices that employ multiple cylindrical members and or complex members may be costly. The present invention recognizes that fewer elements tend to be simpler and more cost effective.

In accordance with an embodiment of the present invention, a needle protective device comprises a needle assembly comprising a needle and a body including first and second locking means, the needle extending from the body along a longitudinal axis. A housing having a chamber receives the body and has a first opening in communication with the chamber along a first axis, the opening is for passing the needle from the received body therethrough. Third locking means are secured to the housing in the chamber along the first axis for engaging the first locking means to retain the body in the chamber on the first axis with the needle projecting through the first opening beyond the housing. Fourth locking means are secured to the housing in the chamber aligned with the first opening on a second axis, the fourth locking means for selectively engaging the first locking means to retain at least a portion of the body and the entire needle within the chamber in response to displacement of the body and needle from alignment with the first axis to the second axis.

In accordance with a further embodiment, body displacement means are movably secured to the housing for displacing the body and needle from the first axis into alignment with the second axis.

In a further embodiment, resilient means resiliently urge the first locking means into engagement with the third and fourth locking means.

In a still further embodiment the housing includes fifth locking means arranged to engage the second locking means on the second axis for axially locking the body in two opposing axial directions.

IN THE DRAWING

FIG. 1 is a plan view of one mirror image half of a housing employing two such halves snap fitted together showing an initial position of a needle cartridge assembly to the housing according to one embodiment of the present invention;

FIG. 1a is an end elevation view of the housing used in the embodiment of FIG. 1;

FIG. 2 is a view similar to that of FIG. 1 in which the cartridge assembly is in the needle use position;

FIG. 3 is a view similar to that of FIG. 2 wherein the needle cartridge has been displaced to a second position immediately prior to automatic retraction of the needle;

FIG. 4 is a view similar to that of FIG. 3 wherein the needle cartridge has been automatically retracted to a protected position;

Figure 5:
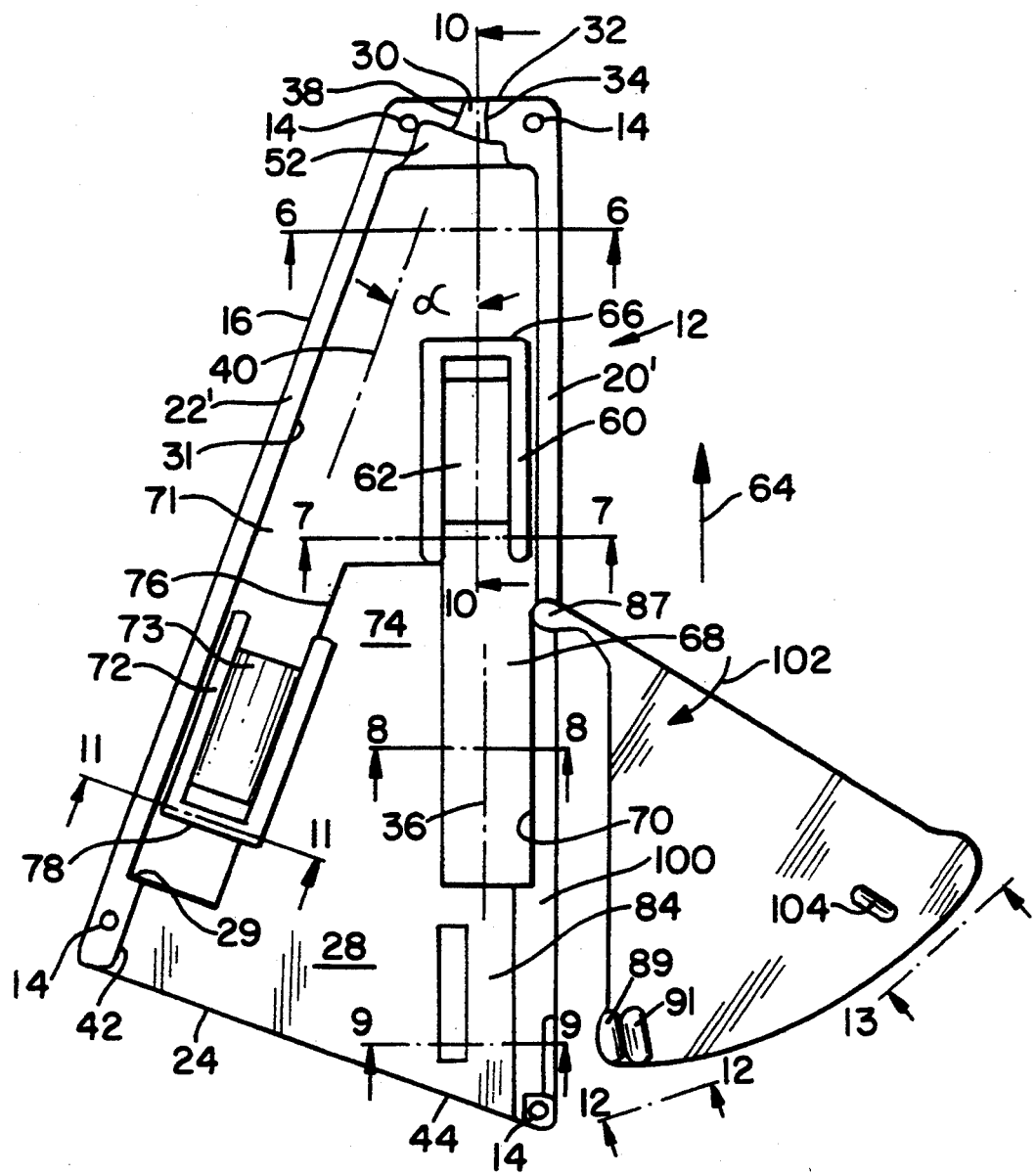
FIG. 5 is an enlarged view of the housing of FIG. 1.

In FIG. 1, device 10 comprises a housing 12 (only one half being shown in FIG. 1) of trapezoidal shape. The housing 12 comprises two mating molded thermoplastic mirror image halves 16 and 18 which snap fit together via projections 14 on half 16 and mating holes (not shown) on the other half 18. The housing 12 has a bottom wall 24 and a top wall 26. Two opposite side walls 20 and 22 are formed by side walls 20' and 22' in half 16 upstanding from bottom wall 24 and walls 20" and 22" in half 18 depending from top wall 26. The walls 18, 20, 22 and 24 form a trapezoidal chamber 28 in the housing. The chamber 28 is in communication with the ambient atmosphere through opening 30 of restricted transverse dimension at end 32 of the housing 12.

Figure 6:
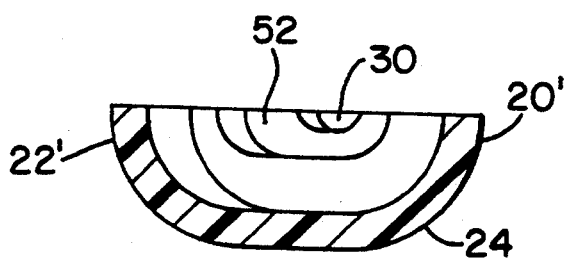
Figure 10:
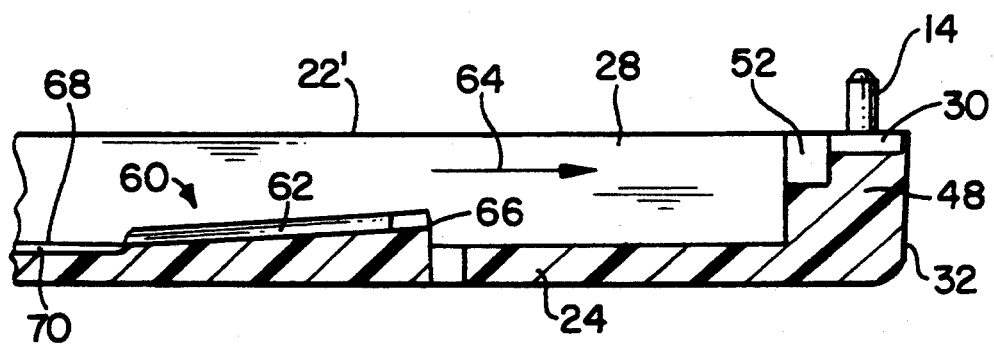

In the following description, the description of half 16 is representative of the other mirror image half 18. In FIG. 5, opening 30 is defined by one side 34 which is parallel to axis 36. Side 34 is an extension of wall 20'. The other side 38 of opening 30 is parallel to axis 40 and wall 22'. In FIG. 10, the bottom wall 24 has an upstanding portion 48 which forms the bottom surface of the opening 30 which is approximately conical. A step 50 is formed in bottom wall 24 and in the side walls 20' and 22' to couple opening 30 to chamber 28 via enlarged chamber 52 (see also FIG. 6). Wall 22' has a shoulder 29 formed by a recess 31 in the wall 22' in chamber 28.

The chamber 28, FIG. 5, is open to the ambient atmosphere at end 44 forming a second opening 42 opposite end 32. The axes 36 and 40 pass through both openings 30 and 42 and subtend an angle $\alpha$.

Figure 7:
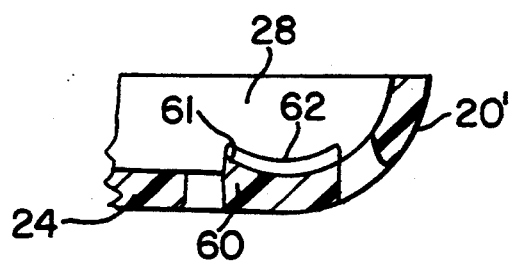

In FIGS. 5, 7 and 10, a ramp 60 is resiliently cantilevered from bottom wall 24 at ramp end 63 by U-shaped slot 61 in the bottom wall 24. Ramp 60 has an arcuate bottom surface 62 and extends in the axial direction 64 parallel to axis 36 from end 63. The ramp 60 in the quiescent state inclines upwardly away from bottom wall 24 in a direction 64 toward end 32, FIG. 10, and terminates in shoulder 66 at a ramp end opposite end 63.

Figure 8:
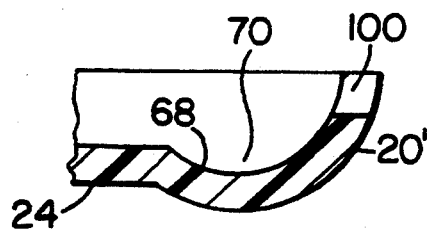

The shoulder 66 is planar and generally normal to bottom wall 24 and axis 36. The bottom surface 62 forms an arcuate channel inclined relative to and generally extending along axis 36. In FIGS. 5, 8 and 10 the surface 62 merges into arcuate bottom surface 68 at end 63. An extended depressed arcuate channel 70, FIGS. 5 and 8, is formed in the bottom wall 24. The bottom wall 24 surface 71 in chamber 28 is depressed with respect to bottom surface 74 forming a tortuous shoulder 76 in the wall 24.

Figure 11:
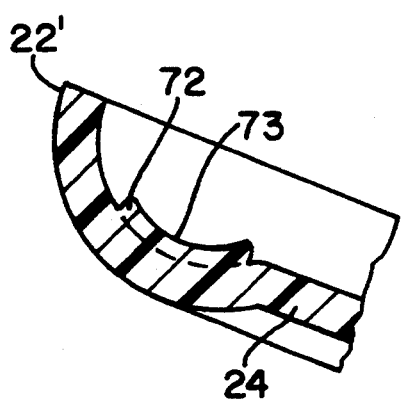
FIGS. 6-13 are respective elevation sectional views of the housing half of FIG. 5 taken along respective lines 6—6, 7—7, 8—8, 9—9, 10—10, 11—11, 12—12 and 13—13.

An second ramp 72 lies on axis 40 resiliently cantilevered from bottom wall 24 end 77 in chamber 28, FIGS. 5 and 11. The ramp 72 is formed by a U-shaped slot 75 in the bottom wall 24 and extends cantilevered from end 77 toward housing 12 end 44. The ramp 72 has an arcuate channel surface 73, FIG. 11 extending along axis 40 and a shoulder 78 at the ramp end formed by slot 75 on axis 40, FIG. 5. The shoulder 78 is planar and generally normal to the bottom wall 24 and axis 40. Ramp 72 is similar to ramp 60 but extends along axis 40 in the generally opposite direction as ramp 60. That is the ramp 72 surface 73 ramps upwardly toward end 44 with shoulder 78 closest to end 44 on the member 72. The ramp 72 resiliently displaces into the drawing plane of FIG. 5 as does the ramp 60 in response to a normal force in this direction.

Figure 9:
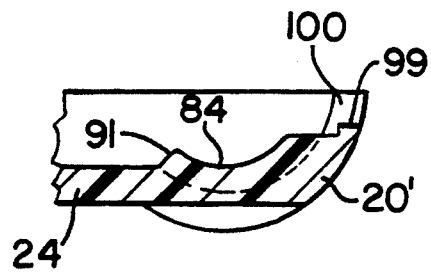

A further arcuate channel 84, FIG. 9 is formed in the chamber 28 surface of bottom wall 24. Channel 84 is aligned on axis 36.

Figure 12:
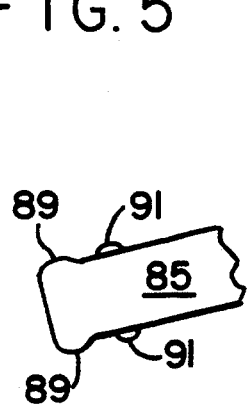
Figure 13:
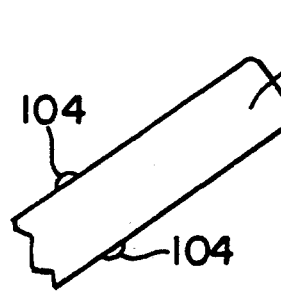

A triangular shaped cam 85, FIG. 5, preferably molded thermoplastic material, has a hinge member 87 which is rotatably secured in a mating hinge opening in wall 20'. The cam 85 has two pairs of projections 89 and 91, FIG. 12, a pair being on opposite sides which form a recess therebetween which snap fit to projections 99, FIG. 9, in opening 100 of the housing 12 wall 20'. Opening 100 receives the cam 85 in response to rotation of the cam 85 about the hinge member 87 in direction 102, FIG. 5. The cam 85 has third projections 104 on opposite sides which snap to projections 99, FIG. 9, when the cam is rotated in direction 102.

In FIG. 1, needle assembly 86 comprises a hollow needle 88 extending from collar 90 secured to body 92. The body and collar are circular cylinders with the collar being of larger diameter forming a shoulder 94 with the body 92. A compression spring 96 encircles the needle 88 and abuts the collar.

In operation, assembly 86 is axially inserted into chamber 28 of housing 12 through opening 44 along axis 36 until the needle 86 protrudes through the opening 30 at end 32, FIG. 2. The body 92 and collar 90 slide along and resiliently depress the ramp 60 on the top and bottom walls. The body 92 rests on the arcuate surface 62 of ramp 60 and is held by the ramp arcuate channel of surface 62 on the axis 36. Recall there are two such ramps on opposite top and bottom walls of the housing 12. In this position, the collar slides along the ramp depressing the ramp 60 until the collar extends beyond the end of the ramp 60 at shoulder 66. At this position the collar drops into the region next adjacent the bottom wall 24 (and top wall 18). The shoulder 94 on the collar 90 engage the shoulders 66 on the ramps 60 (on the top and bottom walls) locking the needle 86 in the extended position of FIG. 2, the shoulders 94 and 66 forming respective first and second mating engaged locking devices for axially locking the assembly 86 in the axial position of FIG. 2. The spring 96 at this time is compressed between end 32 and the collar 90 forcing the collar against the shoulder 66. The compressed spring and the shoulders 94 and 66 thus holds and locks the assembly 86 in this axial position.

After the needle has been used, the cam 85 is rotated in direction 102 until it is in the position of FIG. 3, This displaces the needle assembly 86 into alignment with axis 40 as shown in FIG. 3. The assembly can so displace because the ramp 60 is resiliently depressed in direction 62', FIG. 7, and the body 92 and collar 90 can ride over the lip 61 of the depressed arcuate surface 62 of the ramp 60 and over the lip 91 of the arcuate surface of channel 84, FIGS. 7 and 9. The lip 61 of the arcuate surface 62 (FIG. 7) and lip 91 of surface 84 (FIG. 9) are relatively short in height permitting the body 92 to ride over and pass in the space between the lips on the two halves of the top and bottom walls. This action disengages shoulder 94 on the collar from shoulder 66 on the ramp 60.

The spring 96 is still compressed at this time. The camming action displaces the assembly 86 over angle α onto axis 40. This action depresses the ramps 72 on the top and bottom walls. The body 92 and collar 90 ride over the raised lips of ramp 72 until seated in the arcuate channel 73 of ramp 72 on axis 40.

However, since the needle assembly 86 is no longer held in the axial position of FIG. 3 by the locking action of the shoulders 94 and 66, the assembly 86 is free to displace rearward toward end 44. The assembly 86 is urged rearward toward end 44 by the compressed spring 96. This causes the assembly 86 to displace rearwardly toward end 44 to the position of FIG. 4. In this position, the collar shoulder 94 engages the shoulder 29 in the wall 22' locking the assembly 86 in this rearward position. Also, the collar 90 snaps into position beyond the cantilevered end 78 of the ramp 72 wherein the ramp 72 returns to its original undepressed position. The collar 90 via its extended end 90' in this position is locked axially by the cantilevered end 78 of the ramp 72. The assembly 86 thus can not move forward toward end 32 because the collar end 90' is locked to the ramp end 78. Thus, the assembly 86 can not move axially in the forward and rearward directions on axis 40. The ramp 72 having an arcuate bottom surface 73, FIG. 11, retains the assembly 86 on the axis 40.

It will be appreciated that modifications may be made by one of ordinary skill. It is intended that the detailed description be illustrative and not limiting. The scope of the invention is as defined in the appended claims.

What is claimed is:

1. A needle protective device comprising:
   a needle assembly comprising a needle and a body including first and second locking means, the needle extending from the body along a longitudinal axis;
   a housing having a chamber for receiving the body and having a first opening in communication with the chamber along a first axis, the opening for passing the needle from the received body therethrough;
   third locking means secured to the housing in the chamber along the first axis for engaging the first locking means to retain the body in the chamber on the first axis with the needle projecting through the first opening beyond the housing; and
   fourth locking means secured to the housing in the chamber aligned with the first opening on a second axis, the fourth locking means for selectively engaging the first locking means to retain at least a portion of the body and the entire needle within the chamber in response to displacement of the body and needle from alignment with the first axis to the second axis.

2. The device of claim 1 including body displacement means movably secured to the housing for displacing the body and needle from the first axis into alignment with the second axis.

3. The device of claim 2 including resilient means for resiliently urging the first locking means into engagement with the third and fourth locking means.

4. The device of claim 1 wherein the housing includes fifth locking means arranged to engage the second locking means for locking the needle assembly in opposing axial directions on the second axis.

5. The device of claim 4 wherein the resilient means comprises a compression spring for receiving the needle therethrough such that the spring compresses when the body is on the first axis and expands to push the body away from the first opening and needle out of the first opening along the second axis and into the chamber.

6. The device of claim 1 wherein the first locking means comprises a first shoulder on the body lying in a plane transverse the needle longitudinal axis, and the second locking means comprises a second shoulder on the body, the third and fourth locking means each comprise an abutment secured to the housing and arranged to mate with and engage the first shoulder.

7. The device of claim 1 wherein the body is a circular cylindrical member and the first and second locking means comprises a circular cylindrical collar on the member of larger diameter than the member.

8. The device of claim 6 including fifth locking means secured to the housing, wherein the third and fifth locking means each comprise angularly spaced ramps for axially resiliently receiving the body, the third and fifth locking means comprising a locking shoulder for respectively engaging the body first and second locking means in axial locking engagement.

9. The device of claim 7 wherein the ramps have arcuate body receiving surfaces and are cantilevered from the housing in an axial direction for resilient displacement.

10. The device of claim 2 including means responsive to the displacement of the body from the first to second axes for automatically retracting the needle out of the first opening into the chamber wherein the first locking means disengages the third locking means and engages the fourth locking means, 11. The device of claim 1 wherein the housing has a second opening aligned on and between the first and second axes for receiving the needle and body therethrough on the first axis.

12. The device of claim 2 wherein the displacement means comprises a cam member pivotally secured to the housing for displacement to first and second positions and including means for engaging the body in the first position and manually pushing the body to the second axis when displaced to the second position.

13. The device of claim 12 wherein the cam member is triangular with one apex of the triangle pivotally secured to the housing.

14. The device of claim 13 wherein a second apex of the member and the housing includes further mating locking means for temporarily securing the member to the housing in the first and second positions, 15. The device of claim 8 wherein the ramps form respective channels inclined relative to the corresponding first and second axes.

16. The device of claim 15 wherein the channels are arcuate depressions extending along the corresponding first and second axes.

17. A needle protective device comprising:
a needle assembly comprising a needle and a body including first and second locking means, the needle extending from the body along a longitudinal axis;
a housing having a chamber for receiving the body and having a first opening in communication with the chamber along a first axis, the opening for passing the needle from the received body therethrough, said housing having a second opening for receiving the assembly therethrough on the first axis to place the body in said chamber;
third locking means secured to the housing in the chamber along the first axis for engaging the first locking means to retain the body in the chamber on the first axis with the needle projecting through the first opening beyond the housing;
fourth and fifth locking means secured to the housing in the chamber aligned with the first opening on a second different axis, the fourth locking means for selectively engaging the first locking means and the fifth locking means selectively engaging the second locking means to retain at least a portion of the body and the entire needle within the chamber in response to displacement of the body and needle from alignment with the first axis to the second axis; and
body displacement means movably secured to the housing for displacing the body and needle from the first axis into alignment with the second axis.

18. The device of claim 17 including resilient means for resiliently urging the first and second locking means into engagement with the respective corresponding fourth and fifth locking means.

19. The device of claim 18 wherein the second opening subtends an angular extent including the first and second axes, said body protruding from the second opening when on the second axis.

20. A needle protective device comprising:
a needle assembly comprising a needle and a circular cylindrical elongated hollow core body, said body forming first and second locking means, the needle extending from the body core along a longitudinal axis;
a housing having a chamber for receiving the body along a first axis and having a first opening in communication with the chamber along the first axis, the opening having a restricted transverse dimension for passing only the needle from the received body therethrough, said housing having a second opening for receiving the assembly therethrough on the first axis to place at least a portion of the body in said chamber;
third locking means comprising a projection in the chamber secured to the housing along the first axis for engaging the first locking means to retain the body in the chamber on the first axis with the needle projecting through the first opening beyond the housing;
fourth and fifth locking means in the chamber aligned with the first opening on a second axis, the fourth locking means for selectively engaging the first locking means and the fifth locking means for selectively engaging the second locking means to lock in opposing axial directions at least a portion of the body and the entire needle within the chamber in response to displacement of the body and needle from alignment on the first axis to the second axis;

a spring surrounding the needle and engaged with the received body and housing at said first opening for urging the first locking means in engagement with the third and fourth locking means; and body displacement means movably secured to the housing for manually displacing the body and needle from the first axis into alignment with the second axis such that the spring automatically causes the first locking means to engage the third locking means and the needle to retract into the housing chamber.

* * * * *